United States Patent
De Keersmaecker et al.

(10) Patent No.: US 8,758,688 B2
(45) Date of Patent: Jun. 24, 2014

(54) MICROELECTRONIC STRUCTURES FOR PATTERNED DEPOSITION OF MOLECULES ONTO SURFACES

(75) Inventors: Koen De Keersmaecker, Heverlee (BE); Gustaaf Borghs, Leaven (BE); Piet Herdewijn, Wezemaal (BE)

(73) Assignees: IMEC, Leuven (BE); Katholieke Universiteit Leuven, Leuven (BE)

( * ) Notice: Subject to any disclaimer, the term of this patent is extended or adjusted under 35 U.S.C. 154(b) by 1279 days.

(21) Appl. No.: 10/583,640

(22) PCT Filed: Dec. 22, 2004

(86) PCT No.: PCT/BE2004/000182
§ 371 (c)(1),
(2), (4) Date: Jun. 20, 2006

(87) PCT Pub. No.: WO2005/062049
PCT Pub. Date: Jul. 7, 2005

(65) Prior Publication Data
US 2008/0069971 A1    Mar. 20, 2008

Related U.S. Application Data

(60) Provisional application No. 60/531,931, filed on Dec. 22, 2003.

(51) Int. Cl.
*G01N 27/00* (2006.01)
*B82Y 30/00* (2011.01)
*B82Y 15/00* (2011.01)
*G01N 33/543* (2006.01)

(52) U.S. Cl.
CPC ............... *B82Y 15/00* (2013.01); *B82Y 30/00* (2013.01); *G01N 33/54366* (2013.01)

USPC ........... 422/82.01; 422/50; 422/68.1; 422/56; 427/487; 427/555

(58) Field of Classification Search
USPC ........................................ 422/82.01
See application file for complete search history.

(56) References Cited

U.S. PATENT DOCUMENTS

| 5,466,348 | A | * | 11/1995 | Holm-Kennedy | 205/775 |
| 5,653,939 | A | * | 8/1997 | Hollis et al. | 506/3 |
| 6,078,070 | A | * | 6/2000 | Robinson | 257/280 |
| 2002/0051788 | A1 | | 5/2002 | Pozsgay | |
| 2003/0059807 | A1 | * | 3/2003 | Roach et al. | 435/6 |

FOREIGN PATENT DOCUMENTS

WO    WO 01/84234 A1    11/2001

OTHER PUBLICATIONS

Yousaf et al. May 22, 2001, PNAS, vol. 98 No. 11.*
Shin et al. (Applied Surface Science 214(2003) 214-221).*

(Continued)

*Primary Examiner* — Jill Warden
(74) *Attorney, Agent, or Firm* — Knobbe Martens Olson & Bear LLP

(57) ABSTRACT

The present invention is related to the localized/patterned deposition and/or desorption of (bio)molecules using microelectronic structures. Often pre-existing structures needed for proper functioning of the device (e.g. sensors, . . . ) can be used as individually addressable control structures to achieve localized deposition through thermal and/or electrochemical spotting, thereby reducing the need for and simplifying additional processing steps to achieve localized/patterned deposition. If these multi-purpose structures are not available, additional control structures can be implemented, using microelectronic VLSI production technology.

23 Claims, 4 Drawing Sheets

(56) References Cited

OTHER PUBLICATIONS

Figure 1:
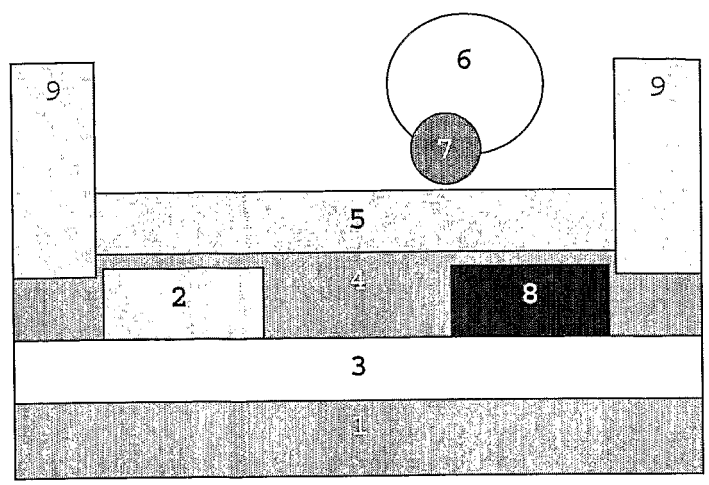

Blawas, A.S., et al. *Protein Patterning*, Biomaterials 19, 1998, pp. 595-609, Elsevier Science Ltd., NSF/ERC Center for Emerging Cardiovascular Technologies, Department of Biomedical Engineering, Duke University, Durham, NC.

Dillmore, W. Shannon, et al. *A Photochemical Method for Patterning the Immobilization of Ligands and Cells to Self-Assembled Monolayers*, Langmuir, 2004, pp. 7223-7231, Department of Chemistry, The University of Chicago, Chicago, IL.

Wu, Ching-Mei, et al. *Immobilization of metallothionein as a sensitive biosensor chip for the detection of metal ions by surface plasmon resonance*, Biosensors and Bioelectronics 20, 2004, pp. 864-871, Elsevier B.V., Department of Life Science, National Tsing Hua University, Taiwan, Republic of China.

Yeo, et al., *Dynamic Interfaces Between Cells and Surfaces: Electroactive Substrates that Sequentially release and attach cells*. Journal of the American Chemical Society, Dec. 10, 2003 vol. 125 No. 49, XP 009055837.

Yousaf, et al, *Using Electroactive Substrates to Pattern the Attachment of Two Different Cell Populations*, Proceedings of the National Academy of Sciences on the USA. May 22, 2001, pp. 5992-5596; SP 002350563.

International Search Report for PCT/BE2004/000182.
Written Opinion for PCT/BE2004/00182.

* cited by examiner

MICROELECTRONIC STRUCTURES FOR PATTERNED DEPOSITION OF MOLECULES ONTO SURFACES

INCORPORATION BY REFERENCE TO RELATED APPLICATIONS

Any and all priority claims identified in the Application Data Sheet, or any correction thereto, are hereby incorporated by reference under 37 CFR 1.57. This application is the national phase under 35 U.S.C. §371 of prior PCT International Application No. PCT/BE04/00182 which has an International Filing Date of Dec. 22, 2004, which designates the United States of America, and which claims priority to U.S. Provisional Application No. 60/531,931 filed Dec. 22, 2003. Each of the aforementioned applications is incorporated by reference herein in its entirety, and each is hereby expressly made a part of this specification.

FIELD OF THE INVENTION

The present invention is related to the field of surface chemistry and more particularly to the localised/patterned deposition of molecules using microelectronic structures.

BACKGROUND OF THE INVENTION

Often molecules have to be adsorbed onto a surface in a localised way. Examples hereof are found in the fields of sensors where in arrays chemical probes or sensitisers are deposited, or in the emerging field of nanotechnology chemical functionality etc.

Techniques for localised deposition or absorption of (bio) molecules include but are not limited to classical lithography (etching or lift-off), direct use of UV light through metal mask or e-beam or laser ablation, soft lithography techniques (micro contact printing, imprinting), micro fluidics, the use of light addressable/activated molecules with lasers/scanning light source like e.g. laser, liquid spotting, . . . . See for instance table 1 of International Patent Application WO 01/84234 and Blawas (1998, Biomaterials 18:595-609). These techniques are well known to a person skilled in the art.

There are several drawbacks or disadvantages coupled to the currently available techniques. These include among others contamination with resists or with solvents used to remove resists, the possible damaging effect of residues to subsequently deposited molecules (e.g. biomolecules sensitive to the presence of organic solvents), the need for intricate/expensive equipment or handling to actually create a patterned chemical surface (e.g. lithography tools, spotting). Micro contact printing, although a simple technique in itself, encounters problems with printing polar moieties and with proper alignment, spotting limited resolution/pitch, etc. In general, expensive tools and equipment are needed.

Adsorption entails physisorption or chemisorption of molecules whereby the latter is preferred from robustness point of view, the possibility of re-use and stability. Examples hereof include in situ synthesis of oligonucleotides on chips, chemisorption via labelled molecules/probes with half of a reactive couple, in situ activation such as NHS/EDC coupling etc.

Possibly, labelling of the molecules can be done before deposition, whereby ex situ purification processes can be used to reduce the deposition process to a one-step process. Efficiency of deposition is often limited with in situ synthesis techniques and/or chemical activation being multi-step processes for adsorption.

There are several methods described in the art that relate to deposition of molecules on a surface and to checking of such binding or deposition. Published US Patent application US 2003/0059807 (Roach et al.), for instance, describes a method for detecting specific interactions between molecules through measuring the heat of binding generated when specific binding pairs interact with each other. The binding event can consist of hybridisation between complementary nucleic acids, but may also consist of other interactions between molecules such as protein/protein, peptide/protein, antigen/antibody (Ag/Ab), protein/DNA interactions or the like. The devices disclosed in Roach et al. measure the heat of binding through arrays of thermistors, possibly integrated in a microelectronic chip or in a multi-well microtiterplate.

International patent application WO 01/84234 (Pieken et al.) describes a novel chemoselective method for immobilising molecules (in particular biomolecules) on a support using cycloaddition reactions such as a Diels-Alder reaction. The support is preferably glass or controlled pore glass. Chemoselectivity is obtained by the chemical nature of the diene/dienophile.

Yousaf and Mrkisch (1999, J. Am. Chem. Soc 121:4286-4287) have described the immobilisation of proteins to electroactive self-assembled monolayers (SAMs) that present a quinone group. In a first step, a mixed monolayer presenting a hydroquinone (HQ) group undergoes oxidation at 220 mV to a quinone (Q) group (and reduction at −150 mV). In a next step, cyclopentadiene (cp), present in an electrolyte solution, reacts with Q via a Diels-Alder reaction.

The Diels-Alder reaction is just one example of a method for bio-immobilisation, well-suited for tailoring monolayers with peptides, carbohydrates and low-molecular weight ligands. This method allows quantitative attachment of groups in low densities and for sequential immobilisation of several ligands to a common substrate (with independent control over the density). Moreover, this method allows for immobilisation of active ligands that can be turned on at discrete times.

Diels-Alder reactions, advantageously, can be carried out in aqueous phase, the Diels-Alder reaction is tremendously accelerated in water and is very fast at room temperature or slightly below.

Published US Patent application US 2002/0051788 (Pozsgay) describes a method for covalently linking biomolecules under neutral conditions using a Diels-Alder reaction. Spontaneous binding between both molecules was here obtained. It was observed that described method provides a degree of control over the rate of coupling between the diene and the dienophile, by modification of the linking moieties. The reaction occurred preferably at or about room temperature.

SUMMARY OF THE INVENTION

The present invention aims to provide a sensing device providing the possibility to detect a specific binding between a recognition molecule and an analyte. Therefore, a sensing device with a plurality of binding sites which can provide control over the binding conditions of an analyte and over the preparation of the binding surface for providing a complete complex assay is needed.

The present invention provides a method to create an organic surface chemistry with patterned functionality by means of individually addressable microelectronic structures, which preferably are already incorporated in the microelectronic device and advantageously can be re-used at later moments for other purposes such as measuring, addressing or controlling or stimulating. Said microelectronic structures locally fulfil, by thermal and/or electrochemical control, the conditions for a chemical adsorption or desorption reaction to occur.

More in particular, the present invention concerns a sensing device for sensing a specific binding between an analyte and a recognition molecule, comprising a sensor with a micro-electronically addressable sensor surface comprising an individually addressable thermal or electrochemical activation element arranged to activate said sensor surface and a recognition molecule bound to said sensor surface by at least a thermal or electrochemical activation step, wherein said sensor is arranged to sense a specific binding between said recognition molecule and an analyte. Therefore, the surface layer provides functions for the anchoring of recognition molecules, preferably covalently in view of reuse and stability. Preferably, the sensing device of the present invention comprises a plurality of micro-electronically individually addressable sensor surfaces, each sensor surfaces being individually activatable. The sensing device can also comprise a plurality of micro-electronically individually addressable sensors for the same sensor surface.

With activated, activatable and activate is meant the local changing of physical or chemical properties of the sensor surface such that said surface is susceptible of binding a recognition molecule on the location where the physical and/or chemical properties have been changed. Said location is called "activatable" when it can be "activated" in the sense of the present invention.

The sensor surface in the device of the present invention preferably comprises an anchoring layer. Said anchoring layer is advantageously selected from the group consisting of chemical molecules or a metal layer. The sensing device of the present invention is preferably characterised in that the anchoring layer is activatable by thermal or electrochemical activation.

Said activation element can be an electrochemical activation element. The sensor surface can comprise a surface layer, the surface layer comprising a material arranged to allow electrontransfer over said surface layer. The material of said surface layer can be selected from the group consisting of metals, thin oxides, semiconductors and organic layer. The surface layer in such cases should allow electron transfer such that the redox reaction to oxidise or reduce a recognition molecule such as e.g. (hydro)quinone can occur. Tunnelling effects typically occur over a few nanometers depending on the strength of the electrical field (up to 5 nm is usual). Semiconductors can be used as good electrochemical activation elements, provided that the energy levels of the redox couple are aligned with the conduction/valence band of the semiconductor, otherwise electron transfer is unlikely to happen. An organic layer can form a tunnelling barrier too, depending on the type of the recognition molecule (e.g. alkane vs. conjugated system). The redox reaction can be controlled by providing a suitable voltage to the electrochemical activation element. Such an electrochemical activation element can be easily provided e.g. with a 3-electrode system in which the surface layer acts as the working electrode, and the surface layer is brought to a certain voltage versus a reference/counter electrode system which determines the voltage of the liquid deposed on the surface layer.

The activation element can be a thermal activation element. Said thermal activation element is preferably selected from the group consisting of resistor, a microwave-heatable element and a peltier element. Preferably, each individual sensor surface is thermally isolated from heat fluxes from neighbouring sensor surfaces. This is preferable as the isolation of individual sensor surfaces allows to create a local and focused hotspot that does not sufficiently warm up neighbouring cold spots that activation of the surface layers occurs at the cold spots. In order to use thermal activation in an efficient way, it is preferable that the sensor surface allows is sufficiently heat-conducting and can withstand temperatures of up to 100° C.

In case Joule dissipation is used for warming up a sensor surface, a sufficient resistance which is electrically accessible should be provided underneath the sensor surface. Preferably, the resistance is electrically isolated from the liquid that is deposited on the sensor surface and is protected from electrochemical corrosion. An example of a suitable material for the resistance is $Ta_2O_5$.

In case the thermal activation element is a microwave-heatable element, the heat is generated by an AC electrical field in an "antenna layer" that emits electrical power which is transformed into heat by dielectric loss in the heat absorbing layer. The heat absorbing layer can be the surface layer or even the deposition liquid, furthermore it does not need to be homogeneous, it can be created by blending in additives with a high dielectric loss factor. The dielectric loss material parameter determines if a layer absorbs microwaves and heats up or not. This allows tailoring the absorption by using different materials to create local hotspots. Penetration depth of the microwave field is important. The antenna layer can be a conductor, a channel layer of a field-effect transistor, but it is important that it is electrically accessible in such a way that an AC electrical field with sufficiently high frequency can be generated in the antenna layer.

The peltier effect or thermoelectric effect can also be used to generate hot spots. In this case two materials with different peltier coefficient are brought into contact with each other and a voltage is applied over this junction. Depending on the direction of the current/voltage, a cooling or heating effect can be obtained. P and N type semiconductors can be used for this purpose. The cooling possibility includes an extra advantage as one can actively exclude some sensor surfaces from activation.

The present invention concerns also the use of a device for localised/patterned deposition and/or desorption of (bio)molecules onto the surface of a device using individually addressable structures wherein the adsorption of deposition and/or desorption if (bio)molecules on said surface is obtained via thermal and/or electrochemical spotting.

Furthermore, The present invention also concerns the use of a microelectronic device for localised/patterned deposition and/or desorption of (bio)molecules onto the surface of a device using addressable microelectronic structures, whereby adsorption or deposition and/or desorption of (bio) molecules on said surface is obtained via thermal and/or electrochemical spotting.

Local heating and/or changes in the oxidation state of molecules, groups or elements of the device will trigger or to the contrary inhibit or prevent binding with complementary molecules that are provided. Thermal and/or electrochemical spotting in the present invention can be used to bind (bio) molecules via chemisorption but also to detach or desorb already bound molecules.

Preferably, the addressable microelectronic structures used for said thermal and/or electrochemical spotting are pre-existing structures of said devices, which are preferably re-used, for instance as sensor, thermistor, . . . .

If required, addressable microelectronic structures or additional addressable microelectronic structures may be implemented in the device using microelectronic VLSI production technology.

Examples of methods to achieve local heating include but are not limited to localised Joule dissipation, laser beam, localised induction heating, heating by peltier elements and localised microwave heating. Joule dissipation may be preferred because of its easy implementation.

Examples of individually addressable structures to achieve electrochemical spotting include but are not limited to conducting microelectrodes, semiconducting microelectrodes, the gate area of a field-effect transistors and the backside of field-effect transistors.

Preferably the (bio)molecules are covalently bound on the surface.

Preferably a Diels-Alder or Michael addition is used to deposit the molecules on the device. These methods can be used to provide a class of dynamic substrates for attached cell culture, wherein the immobilisation of for instance biologically active ligands can be turned on at discrete times. Diels-Alder and Michael addition reactions can occur only if the moieties are in the right oxidation state and if the necessary thermal energy is provided. A Diels-Alder reaction between a hydroquinone and a diene is a good example of a reaction that can be controlled thermally and electrochemically. The documents US 2002/0051788, Yousaf and Mrkisch (1999) and WO 01/84234 are incorporated by reference herein with respect to the reaction parameters (inclusive voltage and temperature) and environment, the preferred molecules. WO 01/84234 is further incorporated by reference herein with respect to some definitions like "diene", "biomolecule" etc.

Examples of reactive groups and their complements used to secure binding are dienes (e.g. cyclohexadiene, cyclopentadiene, . . . ) and dienophiles (e.g. quinone, maleimide, . . . ) for Diels-Alder reactions, nucleophiles (e.g. Ar/R—SH, R—NH$_2$, . . . ) and α, β-unsaturated systems (aldehyde, quinone, maleimide, . . . ) for Michael addition reactions, thiols and metals (e.g. Au, Pt, Cu . . . ) and III-V materials (e.g. GaAs) for thermal desorption and electrochemical ad-/desorption, silanes and metals (e.g. Si, Ti, Ta, Cu, . . . ) and III-V materials (e.g. GaAs) for electrochemical ad-/desorption.

Figure 2:
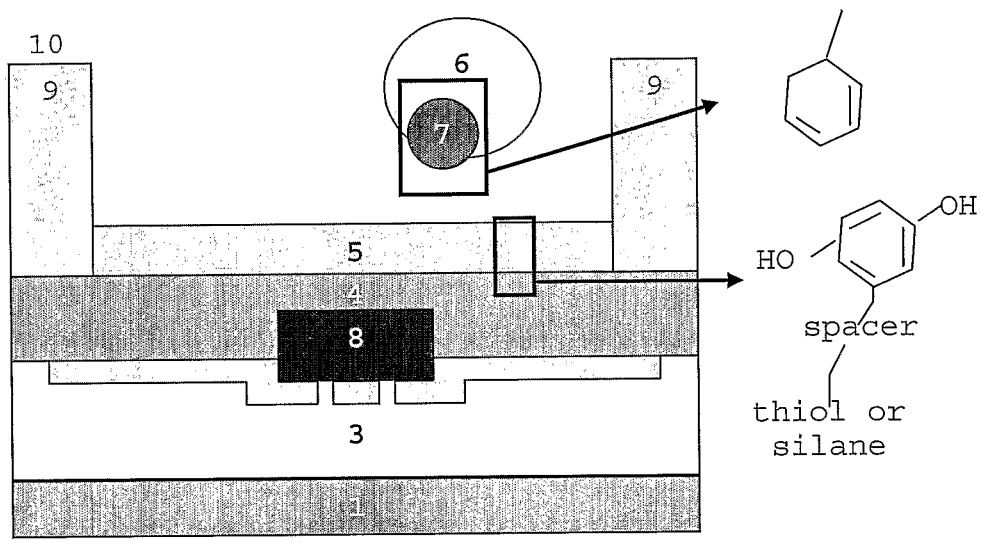
Figure 3:
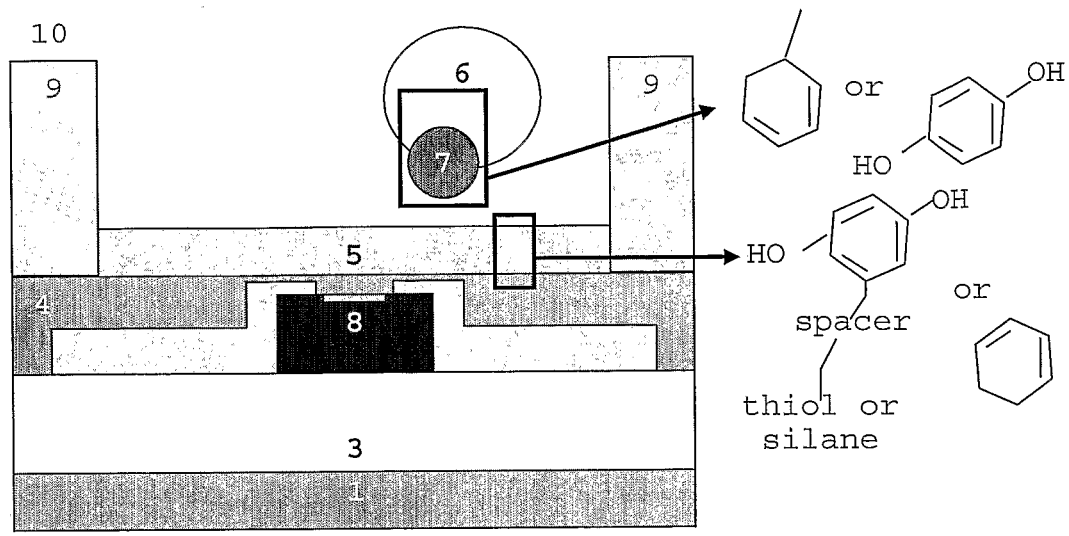

Preferred molecules for deposition of molecules via a Diels-Alder reaction are these shown in FIGS. 2 and 3, wherein molecules attached to the anchoring layer of the device consists of a spacer consisting of S—(CH$_2$)$_n$-hydroquinone, n being between 5 and 20.

Figure 7:
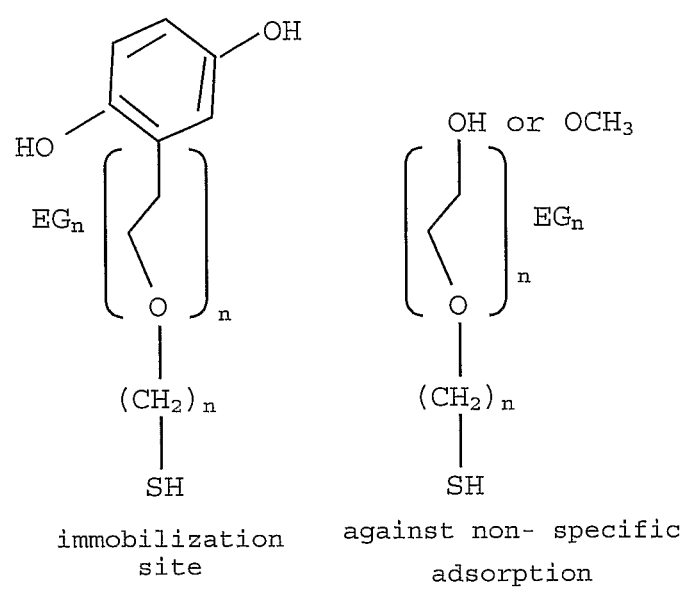

Preferred anchoring molecules used to secure binding and/or to prevent non-specific adsorption of (bio)molecules onto a metal or III-V surface are shown in FIG. 7, wherein EG stands for ethylene glycol and n equals herein preferably 4, 5 or 6.

The present invention further relates to microelectronic devices specifically adapted to perform the above-described desired functions.

The present invention relates for instance to FETs and ISFETS and their use for the above purposes.

The present invention also relates to a method to achieve the above described purposes, said method comprising the following steps:

In a first step, the immobilisation sites of the anchoring layer are activated if they are not inherently reactive. Said activation can be done across the entire device or locally.

In a second step, the molecules are deposited from liquid or vapour phase. Said molecules can be deposited uniformly across the device or can be coarsely localised on the targeted spots by e.g. dispensing from (micro) syringes/pipettes.

In a third step, the reaction conditions are locally satisfied and for an adequate duration the molecules are allowed to react with the immobilisation sites.

In a fourth step, the molecules that have not reacted with the immobilisation sites together with their deposition phase, are removed from the surface of the device by e.g. washing and rinsing.

Next, if multiple types of molecules have to be immobilised, the previous steps are repeated and cycled for every type of molecule. However, if during the first step activation has occurred across the entire device, this step can be skipped in subsequent cycles.

The order of the previous steps can be altered. For example, local activation of the immobilisation site can be done during the third step, just prior to or daring the binding event, after deposition of the molecules. A slightly different cycle is used for desorption processes. Molecules are then allowed to react across the entire device and then desorbed locally.

The present invention also relates to a method to achieve the above described purposes, said method comprising the following steps:

Providing a device, said device comprising a plurality of surfaces wherein at least one surface is individually thermally activatable Activating at least one surface, Depositing molecules onto the at least one surface.

The method can further comprise the step of selecting at least one surface followed by the activation step. The activation step can be performed by using addressable micro-electronic structures or by using laser light.

The device could be a micro-electronic device. The device can comprise at least one addressable structure arranged to individually activate said at least one surface, The method can further comprise the step of cleaning the surface repeating the activation step and the deposition step.

Preferably a cycloaddition reaction such as Diels-Alder or Michael addition is used to deposit the molecules on the device. Diels-Alder and Michael addition reactions can occur only if the moieties are in the right oxidation state and if the necessary thermal energy is provided. A Diels-Alder reaction between a hydroquinone and a diene is a good example of a reaction that can be controlled thermally and electrochemically. The documents US 2002/0051788, and WO 01/84234 are incorporated by reference herein with respect to the reaction parameters (inclusive voltage and temperature) and environment, the preferred molecules. WO 01/84234 is further incorporated by reference herein with respect to some definitions like "diene", "biomolecule" etc.

Examples of reactive groups and their complements used to secure binding are dienes (e.g. cyclohexadiene, cyclopentadiene, . . . ) and dienophiles (e.g. quinone, maleimide, . . . ) for Diels-Alder reactions, nucleophiles (e.g. Ar/R—SH, R—NH$_2$, . . . ) and α, β-unsaturated systems (aldehyde, quinone, maleimide, . . . ) for Michael addition reactions, thiols and metals (e.g. Au, Pt, Cu . . . ) and III-V materials (e.g. GaAs) for thermal desorption and electrochemical ad-/desorption, silanes and metals (e.g. Si, Ti, Ta, Cu, . . . ) and III-V materials (e.g. GaAs) for electrochemical ad-/desorption.

SHORT DESCRIPTION OF THE DRAWINGS

The FIGS. 1-6 present examples of microelectronic devices that can be used to control deposition or attaching of molecules on the surface of the device by thermal and/or electrochemical spotting.

The FIG. 7 presents an exemplary embodiment of an organic anchoring layer for a metal or III-V surface.

DETAILED DESCRIPTION OF THE INVENTION

The present invention discloses a method and microelectronic devices used to control the spatial localisation of molecules on said device by spatially localised thermal and/or electrochemical control over the binding event between said molecules and said device.

Said devices comprise a solid support (1) with one or more individually addressable deposition control structures (2) and an anchoring layer (5) attached to a part of said device that is accessible to (bio)molecules (6) that have to be immobilised onto said device. In order to effect binding onto said device, said reactive functional group and/or are derivatised with at least one reactive moiety (7). Said device can comprise additional functional structures (8), not needed nor used for spatial localisation of said molecules but potentially needed for proper functioning of said device, e.g. sensors.

"Spatially localised thermal control" in the present context is meant to include adjustment of the temperature of a part of the anchoring layer and its immediate surroundings through spatially localised heating or cooling. This method will hereafter be called "thermal spotting".

"Spatially localised electrochemical control" is meant to include adjustment of the oxidation state of a part of the anchoring layer through a locally applied voltage or current. This method will hereafter be called "electrochemical spotting".

Said thermal and/or electrochemical spotting are such that, for the duration of the binding event, adequate values of temperature and/or oxidation state are realised within an area of the anchoring layer surface of less than 1 mm$^2$, hereafter called "a spot", and within a volume of the immediate surroundings, measured extending into the space accessible by said molecules, of less than 1 mm$^3$.

Control over the spatially localised thermal and/or electrochemical state of the anchoring layer and its immediate surroundings is achieved by said individually addressable control structures (2). "Individually addressable" means that the value of controlling parameters (e.g. voltage, current, temperature/joule dissipation) can be set independently for each control structure. Said individually addressable control structures are preferably created by re-using structures that are already present on said device and are required for proper functioning of said device, thereby avoiding the need for additional control structures (e.g. certain sensors, electrical leads, ... )

However, if such multi-purpose structures are not present or their function cannot be reconciled with thermal and/or electrochemical spotting, individually addressable deposition control structures (2) will have to be additionally fabricated on said device. Said deposition control structures (2) are preferably equal in size to or smaller than the "spot" onto which said molecules have to be immobilised. The method of spotting determines the type of said individually addressable control structures possibly to include into the device, whereby it has to be kept in mind that said control structures should best not interfere with proper function of the device itself or its additional functional structures (8). For example, the use of a metal microelectrode for electrochemical spotting might impede with fluorescence detection.

Said microelectronic device, including auxiliary layers (3,4), auxiliary structures (9) and individually addressable control structures (2), are preferably fabricated using microelectronic VLSI fabrication methods as known to a person skilled in the art.

Examples of methods to achieve local heating include but are not limited to localised Joule dissipation (the use of any structure with a resistance R and that carries a current I will heat its environment, examples of dissipating structures/materials that can be made individually addressable and on a local scale include conductors, semiconductors and field effect transistors (FETS)), the use of a locally focused, possibly external, laser beam (which may require the presence of locally constructed mirrors to focus the light beam), localised induction heating, the use of a peltier element and localised microwave heating. These techniques and their conditions of use are all well known in the art. Joule dissipation may be preferred because of its easy implementation.

It is well known that the required power P to raise the temperature of the anchoring layer and its immediate surroundings within a certain time frame, is determined mainly by the material properties (heat capacity, volume, density, thermal conductivity, convection, dielectric loss factor etc) of said device and its surroundings.

Thermal spotting is faced with diffusion of heat into the surroundings. In order to avoid unwanted heating of nearby spots within the timeframe of the binding event, care has to be taking to provide an adequate pitch between the individual spots. Additional thermally isolating structures, e.g. nano-/micro-wells (9) made of thermally isolating material, can for instance be provided to confine the heat flow to the spot where the molecules are to bind.

If needed, multiple sensors can be fit into heating ring which may for instance be put in a microwell in addition to or as alternative to integrated control elements.

Possibly, heating can be controlled for a group of sensors together. The substrate may be made to comprise different layers such that certain parts thereof will act as local hotplates when the entire substrate is placed on a heating source.

"Electrochemical spotting" requires localised control over the oxidation state of electro-active moieties in said anchoring layer by means of applying a voltage in close proximity of or a current through said anchoring layer. Examples of individually addressable structures to achieve electrochemical spotting include but are not limited to conducting microelectrodes, semiconducting microelectrodes, the gate area of a field-effect transistors and the backside of field-effect transistors. Said control structures are preferably positioned underneath said anchoring layer, and have electrical access to said electro-active moieties. Electrical access means an ohmic or diode-like contact to said electro-active moieties in said anchoring layer that allows current to flow to and from the anchoring layer.

Thermal and/or electrochemical spotting might necessitate the use of auxiliary top layers (4) for various reasons. Said auxiliary layer(s) can electrically isolate the channel layer of a field-effect transistor from a liquid/electrolyte. Said auxiliary layer(s) can passivate underlying layers and structures to prevent them from degrading e.g. in wet operating conditions and/or to improve their opto-electronic properties. Said auxiliary layer(s) can cushion the sensitivity of sensor underneath. Said auxiliary layer(s) can provide binding sites for the anchoring layer by creating a surface more susceptible to an appropriate type of surface chemistry treatment. Said auxiliary layer(s) can improve heat conduction from the temperature control structures towards the anchoring layer and/or control heat spreading such that the temperature uniformity of the anchoring layer is improved. Said auxiliary layer(s) may not impede with proper functioning of the control structures. For example in the case of electrochemical spotting, an oxide layer on a metal microelectrode can provide binding sites for a silane-immobilised anchoring layer. However this oxide layer must then be thin enough to allow current to tunnel through (i.e. ohmic contact) such that the oxidation state of the anchoring layer can be electrochemically altered by the control structure underneath.

Auxiliary bottom layers (3) may be needed to thermally or electrically isolate the control structures and anchoring layer from the solid support (2), or to glue/bond said control structures and auxiliary layers onto a solid support (2). Depending on their intended function, the characteristics and materials of the auxiliary layers can be adapted.

The anchoring layer (5) functions as an interface between the device and the molecules that have to be immobilised (6). Said anchoring layer therefore will have at least one functional group that binds to the surface of the device—i.e. to the auxiliary layer (4), or directly to the individually addressable control structures (2), or to the additional functional structures (8)—and has at least another functional group that, in its native form and/or after derivatisation, specifically binds to the reactive moiety (7) of said molecules (6).

The anchoring layer (5) can be a layer comprising organic molecules such as self-assembling monolayers (SAMs) or mixed self-assembling monolayers with appropriate chemical functions for the anchoring layer to adhere to the surface of the device and for said molecules (6) to specifically bind to the anchoring layer. Said anchoring layer can comprise subsequently applied multiple layers with or without chemical reactive interlayer. Said anchoring layer can also be a gel or a polymer (non-conductive or conductive). Said anchoring layer can also be an inorganic oxide layer such as $SiO_2$, $Ta_2O_5$, . . . , or can be a noble metallic layer such as Au, Pt, . . . , or can be an oxidisable metallic layer such as Ta, Ti, . . . , or an oxidisable semi-metallic layer such as Si, . . . , or a III-V layer such as GaAs, . . . .

When the anchoring layer is not an organic layer but e.g. a noble metal such as Au, the Au electrode can be biased such that thiols cannot bind to it and/or will desorb. A Ta electrode can be electrochemically oxidised/reduced such that silanes bind or cannot bind to it (depending on the presence of Ta oxides). Alternatively, biomolecules can be derivatised with for instance a thiol or silane, or one can work via intermediate cross-linkers. These examples are given to demonstrate that the method according to the present invention is widely applicable and can cover any type of chemisorption or desorption initialised by and/or dependent from a given temperature condition and/or oxidation state. The method is thus not restricted to deposition of (bio)molecules via a Diels-Alder reaction.

Organic adhering chemical functions are determined by the nature of the surface. For instance, silanes may be adhered on oxide surfaces (e.g. $SiO_2$, $TiO_2$, $Ta_2O_5$), thiols on metals (e.g. Au, Pt) or III-V materials (e.g. GaAs), carboxylic acids on metal oxides or on III-V materials, sulfonates ($SO_3$—) and phosphonates ($PO_3$—) on III-V materials.

Said immobilising chemical functions are determined by the reaction scheme used to have said molecules bind specifically with or to said anchoring layer. Said immobilising reaction scheme is chosen such that the binding event is specific and can be inhibited or triggered by local control of the temperature and/or oxidation state of the immobilisation sites or their immediate surroundings.

Said control is exerted and localised by means of the individually addressable control structures. The immobilisation sites can be reactive in their native form and/or can be made reactive after derivatisation. Examples of immobilisation reactions include but are not limited to Diels-Alder and Michael addition reactions, thermal desorption, electrochemical desorption and electrochemical adsorption. In said immobilisation schemes, an additive/binding or disruptive reaction occurs between two complementary chemical functions.

Non-restrictive examples of immobilisation sites or reactive groups and their complements are dienes (e.g. cyclohexadiene, cyclopentadiene, . . . ) and dienophiles (e.g. quinone, maleimide, . . . ) for Diels-Alder reactions, nucleophiles (e.g. Ar/R—SH, R—$NH_2$, . . . ) and α, β-unsaturated systems (aldehyde, quinone, maleimide, . . . ) for Michael addition reactions, thiols and metals (e.g. Au, Pt, Cu . . . ) and III-V materials (e.g. GaAs) for thermal desorption and electrochemical ad-/desorption, silanes and metals (e.g. Si, Ti, Ta, Cu, . . . ) and III-V materials (e.g. GaAs) for electrochemical ad-/desorption.

The method of spotting determines which part of the complementary functions has to be located on the surface of the device. For example, electrochemical spotting requires an electro-active moiety as immobilisation site in the anchoring layer, such as hydroquinone/quinone, but also $Ta/Ta_2O_5$, $Ti/TiO_2$, $Si/SiO_2$, Cu/Cu-oxide, GaAs/GaAs-oxide, . . . . On the other hand, thermal spotting poses less restrictions to which part of the complements is located on the surface, e.g. for a thermally controlled Diels-Alder reaction either the diene or the dienophile can be located on the surface. Furthermore, chemical compatibility issues during deposition of the anchoring layer and immobilisation of said molecules (6), determines which part of the complements has to be located on the surface of the device.

The reactive counterpart (7) of the complementary chemical functions to immobilise said molecules (6) onto the device can be inherently present in said molecules and/or can be implemented by synthesis/derivatisation. Chemical compatibility issues between the reactive moiety (7) and the rest of the molecule again determine which part of the complements can be synthesised onto said molecules.

Incorporating organic surface chemistry into the inorganic semiconductor process flow—including front-end, back-end and packaging—raises an entirely new set of constraints.

Several factors have to be taken into account when scheduling the various inorganic and organic process steps. Applied materials wetted during the various surface modifications should be compatible with the chemical processes involved and should be able to withstand possibly harsh chemical environments. Current and subsequent organic and inorganic process steps should be checked for temperatures and temperature budgets.

When designing the hybrid process flow, the main goal should be to use standard (packaging) materials and process steps as much as possible.

For instance, biomolecules, mainly proteins, and some functional molecules limit the maximum process temperature since they tend to denature and/or loose their function when the temperature is raised too high. On the other hand, some standard packaging techniques, such as flip chip assembly, involve temperatures as high as 350° C.

Finally, a lot of semiconductor materials/devices have a limited temperature budget: they can withstand a certain temperature only for a limited time before electronic properties start to degrade (e.g. because of diffusion). Hence, not only maximum temperature but also the time required for chemical synthesis can become a critical parameter. A person skilled in the art, will know how to deal with these matters.

The devices and methods that are provided in this invention offer a variety of advantages over the prior art. Localised/ patterned deposition as provided in this invention is self-aligned, thereby avoiding the need for aligned masking steps, which require intricate machines and may contaminate and/or damage the applied surface chemistry. Said devices and methods allow for localised/patterned deposition of molecules by easy electronic/electrical control Therefore no sophisticated machines are needed to achieve localisation. As disclosed in this invention, often pre-existing structures needed for proper functioning of the device (e.g. sensors, . . . ) can be used as individually addressable control structures to achieve localised deposition, thereby reducing the need for and simplifying additional processing steps to achieve localised/patterned deposition. And if these multi-purpose structures are not available, additional control structures can readily be implemented, using microelectronic VLSI production technology. This enables mass production and thus reduces cost or limits additional cost. Furthermore, using VLSI produced structures to localise deposition, assures adequate resolution of the deposited surface chemistry patterns. Ex-situ derivatisation of molecules with reactive binding complements facilitates purification, and allows said molecules to be immobilised in a one-step reaction, which is beneficial for the efficiency of the immobilisation binding event. Finally, the disclosed method of localised deposition and the microelectronic nature of the disclosed device can be easily scaled to pattern surface chemistry on large arrays of functional elements.

The surface layer has to provide functions for the anchoring layer to attach to (preferably covalently in view of re-use and stability).

Specifications of the surface layer/device in view of spotting/deposition can be summarised as follows:

Electrochemical Spotting (ES):

For electrochemical spotting, the surface layer has to allow electron transfer such that the redox reaction to oxidise/reduce (hydro)quinone can occur. Examples of such surface layers are metals, thin oxides (tunnelling typically occurs only over a few nanometer (up to 5 nm), but this depends on the strength of the electrical field), semiconductors (but then there is a requirement that the energy levels of the redox centre are aligned with the conduction/valence band of the semiconductor, otherwise electron transfer is unlikely or better less likely to happen). The organic anchoring layer can form a tunnelling barrier too, depending on the type of the spacer (alkane versus conjugated system). The device and surface layer should be electrically accessible such that a voltage can be applied so that the redox reaction can be controlled.

Thermal Spotting (TS):

The surface layer has to allow heat flux to pass through, and should be able to withstand temperatures up to about 100° C. Heat created in the local hotspot has to remain focused so that a nearby cold spot doesn't heat enough for the D-A or Michael addition reaction to occur, passive/active thermal isolation should be provided.

The following characteristics should be considered for the different types of thermal activation elements:

Heat Generated by Joule Dissipation:
- heat power=(current in the heat generating layer)$^2$×(resistance of the heat generating layer)
- the surface layer or one of the layers underneath has to be electrically accessible and has to have a sufficient resistance (determined by resistivity of the material and geometrical design of the layer/device) such that a current can flow into that layer and generate enough power preferably without exceeding the current density limit of the material.
- if the heat is generated not in the surface layer, all layers in between the surface layer and the heat generating layer should allow the heat flux to pass efficiently.
- thermal conductance of the layer(s) determines the efficiency of heat transfer
- the heat generating layer (i.e. the layer in which the current flows) is preferably but not necessarily electrically isolated from the deposition liquid, and protected from electrochemical corrosion
- Ta2O5 can be used as an example of a suitable material since it is a readily used material in microelectronics that is electrically isolating, offers quite stable protection against electrochemical corrosion and has a rather good thermal conduction for an oxide.

Heat Generated by Microwave:
- heat is generated by an AC electrical field in the "antenna layer" that emits electrical power which is transformed into heat by dielectric loss in the heat absorbing layer.
- Power=$2\pi \times \epsilon_0 \times$frequency×(dielectric loss factor, i.e. imaginary part of complex permitivity)×(electrical field strength)$^2$
- heat absorbing layer can be the surface layer or the deposition liquid; the heat absorbing layer doesn't have to be a homogenous substance: additives with a high dielectric loss factor can be blended in
- material parameter dielectric loss (DL) determines if a layer absorbs the microwave field and heats up or not. One can tune the absorption by selecting various materials with different DL and create local hot spots; however heat generated in these hotspots will still diffuse out if no isolation structures are provided.
- penetration depth (PD) plays crucial role: distance over which microwave power can propagate before it is absorbed; PD depends on the dielectric properties of the material and is inversely proportional to the frequency of the electrical field; playing around with materials with different dielectrical properties can help to tune absorption and create local hotspots
- antenna layer should be electrically accessible in such a way that an AC electrical field with high enough frequency can be generated in the antenna layer.
- antenna layer can be a conductor, the channel layer of a field-effect transistor Heat Generated by Thermoelectric Effect:
- i.e. peltier effect; two materials with different peltier coefficient are brought into contact with each other or via a conductor; a voltage is applied across this junction; depending on the direction of the current/voltage, the junction can be heated or actively cooled
- heating/cooling power=(difference in peltier coefficients)×current
- peltier coefficient, electrical conductivity and thermal conductivity determine the quality of a material to be used as thermoelectric material
- suitable material: p and n type semiconductor
- active cooling helps dramatically to localise heating.

The detecting capabilities that can be implemented on the device of the present invention can comprise the following:

a. Optical—Fluorescence:
- in order to avoid quenching, the type of material of the surface layer and the distance between the surface layer and the fluorophore is important.
- e.g. gold (used for e.g. the working electrode in ES, or as joule dissipator in TS) quenches fluorescence of common fluorophores used in biotech→get fluorophore farther away/far enough (typically >20 nm) from gold by putting non-quenching layer (anorganic layer or spacer of anchoring layer) in between. Care should be taken that electron transfer should still be feasible or heat flux should not be hindered too much.

b. Optical—Calorimetric
c. Electrical—Impedance
   e.g. interdigitated electrodes (IDE)
   metal IDE=molecules anchoring layer directly on metal can be used for electrochemical spotting (use IDE fingers as working electrode in 3-electrode setup, biasing similar to drawing of voltammetric electrochemical spotting for voltammetric sensor but in this case the working electrode consists of 2 sets of fingers of the IDE, isopotentially biased) or thermal spotting.
   oxide covered IDE: thin oxide electrochemical spotting is still feasible; thermal same remarks as previous.
d. Electrical—Voltammetric:
   the surface layer should be electrically accessible so that the redox reactions occurring at the probes can be monitored. This also puts constraints on the spacers in the anchoring layer (tunnelling/conduction)
   e.g. a simple electrode can be used to electrochemically or thermally spot the redox active probe and to monitor the redox reaction in a voltammetric setup; double use means biasing the same structure in a different way depending on spotting or sensing mode. Biasing for sensing mode is known to person skilled in the art.
e. Electrical—Amperometric
   cf. voltammetric: same for spotting but a different way of biasing for sensing (known to person skilled in the art) is used.
f. Electrical—Field-Effect:
   the dielectric constant of the surface layer is important to ensure a good capacitive coupling between charge immobilised at surface (by specific recognition event) and mirror charge underneath in e.g. the channel of a field-effect transistor (FET)
   the biasing for spotting depends on the type of FET
   e.g. for a classic single gate ISFET/CHEMFET an anchoring layer is immobilised on top of dielectric of the non-metallised gate area, thermal spotting can be used by biasing the ISFET so that drain source current flows which causes heating up of the transistor since the channel has resistance (value of which is controlled by gate source bias); biasing can be dome via a reference electrode in deposition liquid. This will however bias the gate-source voltage for all transistors on the chip, one can use the drain source voltage to control the drain source current flow.
   For a single gate ISFET with metal floating gate, an anchoring layer on metal floating gate can be provided. Thermal activation still works similar to previous ISFET embodiment (slightly different values for voltages), however, the floating gate can be contacted by a switch transistor from outside so that electrical access can be established during spotting, and electrical access can be severed during sensing so that the gate becomes floating again, which makes electrochemical spotting possible.
   e.g. dual-gate ISFET: anchoring layer immobilised on the oxide on the back gate; same considerations as with classic single gate ISFET, however due to second gate, transistor can be individually biased by $2^{nd}$ gate to control drain source current (for thermal spotting)
   e.g. dual gate ISFET with floating metal gate: same as with single gate: switch transistor possible apart from thermal spotting
   consideration: depending on the required heating power, a large current might be required (since the resistance of the channel can be varied only in limited way by the gate source voltage and current is squared in power formula), however for sensing, a lower base current is preferred. Biasing between 2 regimes with gate source voltage can be used; this is feasible with all types of CHEMFETs (both single and dual gate).
g. Electrical—Change in Work Function
   e.g. anchoring layer on bare semiconductor layer of FET; this type of sensor can also measure the field effect of specifically immobilised charge by a recognition event.
   bare semiconductor can be used for thermal spotting without too many constraints (similar as for typical ISFET above)
   however since anchoring layer can be on the bare semiconductor, electrochemical spotting becomes more feasible; no special constraints except for the ones mentioned before (alignment of energy levels, possibly use of mediators needed), only special biasing: semiconductor channel of FET can be used as working electrode in 3-electrode setup by isopotentially biasing source and drain contact vs. reference electrode in deposition.
   can be done for single and dual gate device.
h. Magnetic
   surface layer shouldn't shield the magnetic field; probably auxiliary structure needed to heat.
i. Calorimetric

EXAMPLES

The following preferred embodiments and working examples are only meant as illustrations of how microelectronic structures can be used to create localised and patterned deposition of molecules. They are not to be interpreted as exclusive or limiting.

Example 1

FET Transistor

In a first embodiment, a device is disclosed as in FIG. 2. Said device comprises a field effect transistor (FET) (8)—e.g. a MOSFET, a MESFET, a HEMT or a TFT, . . . —that is flipped upside down and is glued onto a host substrate (1). The anchoring layer (5) can be immobilised directly onto the backside of the FET or onto an auxiliary top layer (4). Wells (9) can be created on the surface of said device to confine the heat flow for the duration of the binding event that occurs between molecules (6) and the anchoring layer (5). Said wells can also reduce the required volumes of said molecules (6) for immobilisation by enabling coarse localisation through dispensing.

In this first embodiment said FET can simultaneously function as a sensor (to detect charges, charge distributions, electromagnetic fields, . . . ) and as an individually addressable control structure to localise deposition. However, said FET can also be used solely as an individually addressable control structure to spot molecules. Said FET can accomplish thermal spotting (by e.g. Joule dissipation or by microwave heating) and/or electrochemical spotting (by e.g. serving as a working electrode in a voltammetric setup). Furthermore, both methods can be combined to improve spotting control. Depending on the intended spotting method, the characteristics/dimensions and materials of the auxiliary layers (4) and (3), and of the anchoring layer (5) can be adapted.

Referring to the first embodiment as shown by FIG. 2, the FET can be made using Si, Ge, III-V, polymer, . . . semiconductor technology. Its exact structure and materials will differ depending on the type of field effect transistor. The auxiliary bottom layer (3) can comprise a polymer, such as BCB, SU-8, . . . and can thus function as a glue layer between the FET and the host substrate (1). Furthermore, said auxiliary bottom layer can be chosen to reduce the heat flow in lateral and downward direction, and to optimise heat transfer towards the liquid environment (10), in which case its thermal properties become important, like e.g. having a high thermal resistivity. The auxiliary top layer (4) can be implemented for various reasons. Said auxiliary top layer can be introduced to cushion the signal, i.e. to reduce the sensitivity of the device. It might be needed to protect said FET from degradation or to electrically isolate the FET from the liquid. Said auxiliary top layer may help to create a surface more susceptible to an appropriate type of surface chemistry treatment. The auxiliary top layer may also help to improve heat conduction from the heat source, i.e. the FET, towards the anchoring layer (5) and its immediate (liquid) environment (10). Furthermore, in order to facilitate electrochemical spotting, the auxiliary top layer may help to overcome energetic misalignment between the band structure of the semiconductor in the FET and the HOMO/LUMO levels of the electro-active moieties in the anchoring layer (5). Depending on its intended function, the characteristics/dimensions and materials of the auxiliary top layer can be adapted. This can easily be done by a person skilled in the art. However, said auxiliary top layer preferably may not impede with proper functioning of the FET as a sensor and/or, if wished for, as a control structure for electrochemical spotting. In order not to reduce capacitive coupling of the signal to the channel of the FET, the auxiliary top layer preferably has a high electric permitivity. In order to allow electrochemical spotting, a potentially dielectric auxiliary top layer has to be thin enough—preferably less than 10 nm—to allow electrical access by tunnelling to the anchoring layer. Said auxiliary top layer can comprise a metal layer, such as Pt, . . . and/or a dielectric layer. Since it combines a high dielectric permitivity with a good thermal conductivity, and is very stable against electrochemical corrosion, even as a thin layer, this dielectric layer would preferably, but not-restrictively, be $Ta_2O_5$. The wells (9) can comprise polymers that are processed in-situ on said device, such as BCB, SU-8, polyimide, parylene, teflon, . . . , or can for instance be implemented using nano-/micro-titer plates.

In reference to FIG. 2, the anchoring layer (5) of the first embodiment should provide at least some but not necessarily all of the following functions:
a) an intimate and stable binding to the surface of the device—i.e. to the auxiliary layer (4), or directly to the individually addressable control structure/the additional functional structure (8), the FET—to assure robustness, long-term stability, and potential re-usability,
b) adequate passivation and protection of the surface,
c) a tailored influence on the opto-electronic properties of the semi-conducting channel layer of the FET underneath in order to tune the response of the FET sensor,
d) a reactive site that binds to the molecules (6), which have to immobilised onto said device, via a reaction scheme that is chosen such that the binding event is specific and can be inhibited or to the contrary triggered by local control of the temperature and/or oxidation state of said reactive immobilisation site or its immediate surroundings,
e) a molecular function to allow or facilitate electrical access to electro-active moieties, e.g. conjugated systems and mediators, and
f) a molecular function to prevent non-specific adsorption to reduce noise from adsorbing non-targeted analytes.

Still in reference to the first embodiment (FIG. 2), the multifunctional anchoring layer (5) comprises a surface adhering functional group that preferably binds the anchoring layer covalently or coordinatively to the surface of said device. The surface adhering functional group of an organic anchoring layer can be chosen to be e.g. a thiol, a silane, . . . depending on the nature of the surface. Preferred, but non-restrictive examples of such reaction schemes for immobilisation of the molecules (6) are Diels-Alder and Michael addition reactions. In said immobilisation schemes, an additive binding reaction occurs between two complementary chemical functions. Non-restrictive examples of immobilisation sites and their complements are dienes (e.g. cyclohexadiene, cyclopentadiene, . . . ) and dienophiles (e.g. quinone, maleimide, . . . ) for Diels-Alder reactions, nucleophiles (e.g. Ar/R—SH, R—$NH_2$, . . . ) and $\alpha,\beta$-unsaturated systems (aldehyde, quinone, maleimide, . . . ) for Michael addition reactions. Preferably dienophiles/$\alpha,\beta$-unsaturated systems make up the immobilisation sites, since they are electro-active moieties and thereby enable both thermal and electrochemical spotting. Their complements—the dienes and nucleophiles—are, if not inherently present, synthesised onto the molecules (6). The spacers of the organic anchoring layer can comprise aliphatic and/or aromatic moieties, but, unless they are conjugate systems, they should be limited in length if electrochemical spotting is aspired. In order to enable electron-transfer, chemical functions can be incorporated into the organic anchoring layer to overcome misalignment of the energetic band structure of the FET and the HOMO/LUMO energy levels of the electro-active moieties. The nature of these chemical functions is determined by the electro-active moieties and the surface of the FET.

Subsequent embodiments differ mainly in the implementation of the microelectronic structures. Unless stated otherwise, the same issues apply as mentioned for the first embodiment. In reference to the subsequent figures, the same numbering for the same constitutional parts has been used.

Example 2

ISFET Transistor

A second embodiment of the present invention is illustrated in FIG. 3. The disclosed device comprises an ion sensitive field effect transistor (ISFET) (8)—based on a MOSFET, MESFET, HEMT or TFT, . . . type of transducer—that is made on a solid support (1). Said ISFET device can be a standard configuration with an exposed gate, or a configuration using an exposed floating gate. Unless stated otherwise, both configurations will hereafter be referred to as an exposed gate area configuration, not discerning if the gate is floating. The anchoring layer (5) can be immobilised directly onto the exposed gate area of the ISFET or onto an auxiliary top layer (4). Wells (9) can be created on the surface of said device for the same reasons as mentioned in the first embodiment.

In this second embodiment said ISFET can simultaneously function as a sensor (to detect charges, charge distributions, electromagnetic fields, . . . ) and as an individually addressable control structure to localise deposition. However, said ISFET can also be used solely as an individually addressable control structure to spot molecules. Said ISFET can accomplish thermal spotting by Joule dissipation and/or by microwave heating. Due to the characteristics of the exposed gate area, said ISFET is less suited for electrochemical spotting. Indeed, an ISFET requires a dielectric top layer in the exposed gate area as the active sensitive part of ISFET. Said dielectric top layer is generally quite thick, usually more than 10 nm, and thus hinders electrical access to the anchoring layer (5). Furthermore, any current drawn through said dielectric top layer, would probably damage said dielectric top layer and thus be detrimental to the sensor operation of said ISFET.

Referring to the second embodiment as depicted in FIG. 3, the ISFET can be made using Si, Ge, III-V, polymer, . . . semiconductor technology. The auxiliary bottom layer (3) may be implemented to optimise upward heat transfer by posing a highly resistive thermal path downward and/or in lateral direction. The auxiliary bottom layer (3) can be incorporated during processing of said ISFET by deposition, epitaxy or any other technique known in the art. In order to create a thermally isolating layer said auxiliary bottom layer can comprise materials such as SiO2, Si3N4, implanted SiO2, low temperature grown undoped GaAs, . . . . The auxiliary top layer (4) can be implemented for the same reasons as stated for the first embodiment, however, with exception of the electrochemical spotting issues, since said ISFET is less suited for this method of spotting. Due to its material characteristics, as mentioned for the first embodiment, $Ta_2O_5$ is again a preferred, albeit not restrictive choice of material for said auxiliary top layer. Furthermore, $Ta_2O_5$ exhibits beneficial characteristics (high pH sensitivity, i.e. high density of binding sites for $H^+/OH^-$, improved drift characteristics) that may improve the sensitivity and operation of said ISFET.

The anchoring layer (5) of the second embodiment is subject to same requirements and specifications as in the first embodiment. Again, Diels-Alder and Michael addition reactions are the preferred immobilisation schemes for the molecules (6), and thus similar chemical functionalities as in the first embodiment should be incorporated in said anchoring layer. However, since electrochemical spotting is a lesser option for the ISFET, less restrictions are imposed for choosing which part of the immobilisation complements (diene/dienophile, nucleophile/$\alpha,\beta$-unsaturated systems) should be located on said anchoring layer. The immobilisation site does no longer have to be electro-active, and can therefore be chosen more easily to comply with chemical compatibility issues. Also the characteristics of the spacers (length, nature of chemical functionality) can be less stringent.

Example 3

Separate Deposition Control Structures

Figure 4:
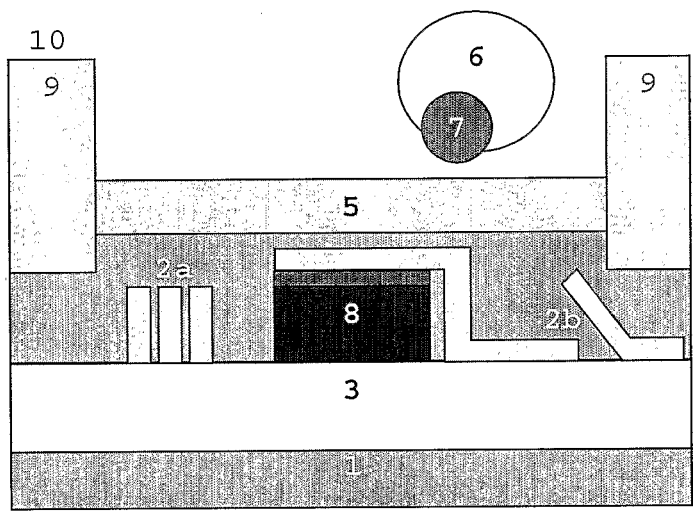
Figure 5:
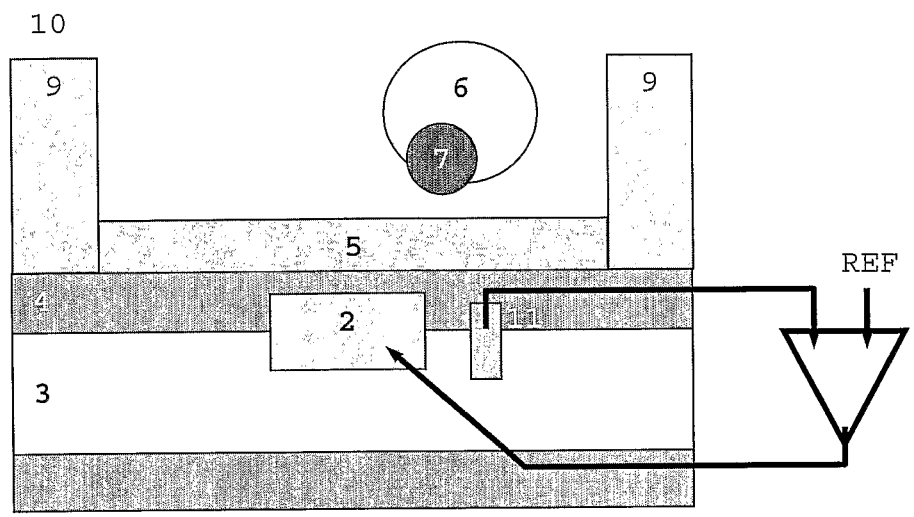

FIG. 4 depicts a third embodiment of the present invention. In this embodiment deposition control structures (2a, 2b) are implemented separately from the functional structures (8). Non-restrictive examples of deposition control structures are Joule dissipative heaters, peltier elements as temperature control elements (2a), and switched or non-switched microelectrodes (2b) to control the oxidation state of electro-active moieties in the anchoring layer (5). Non-restrictive examples of functional structures (8) are the flipped FET and the ISFET from the first and second embodiment, photodetectors, . . . . If the thermal and/or electrochemical spotting methods interfere with or cannot be reconciled with proper functioning of said functional structures (8) or of the entire device, additional deposition control structures (2) should be implemented separately. For example, due to being designed for sensor operation said FET or ISFET might not be able to draw enough current to adequately heat the anchoring layer and its immediate surroundings. As another example, as mentioned in the second embodiment said ISFET is usually not compatible with electrochemical spotting. But, an externally switchable/accessible microelectrode implemented as floating gate on the exposed gate area of the ISFET could overcome this deficiency. As a last example, a photodetector based sensor system is mentioned, in which the sensor element, i.e. the photodetector, hardly allows any method of in-situ spotting. However, a transparent microelectrode (comprising e.g. indium tin oxide) on top of the photodetector would, depending on its configuration, enable thermal and/or electrochemical spotting, without interfering with its ability to capture light. For specific materials to implement temperature control elements and/or microelectrodes for electrochemical spotting, see the fourth and fifth embodiment.

Example 4

With Local Temperature Sensor

In a fourth embodiment (see FIG. 5) localisation of molecules is achieved through thermal spotting by means of local temperature control elements (2), implemented on a solid substrate (1). Non-restrictive examples of temperature control structures are Joule dissipative heaters, peltier elements and microwave heaters. A local temperature sensor (11) can be integrated to monitor the heating/cooling process and provide control feedback for the applied thermal power. Said temperature sensor, such as e.g. a resistance temperature detector (RTD) a thermistor, a thermocouple or a diode, can be implemented separately from the local temperature control element (2), or the local temperature control element (2) itself can be used as a temperature sensor. An example of the latter implementation is a Pt microelectrode, which can simultaneously serve as a Joule dissipative heater and as a RTD. Since heat tends to diffuse throughout the device, care has to be taken that the device is designed such that, for the duration of immobilisation binding event, temperature changes are confined to a predetermined spot. In that way, the temperature of neighbouring spots does not reach the reaction threshold, and thus the binding event is inhibited. In order to meet said specification the physical dimensions of said device and its substructures are paramount, especially the distance, i.e. the pitch, between said temperature control elements. Furthermore, auxiliary layers and structures can be implemented to relax the thermal specifications and to decrease as such said pitch. An auxiliary bottom layer (3) can be incorporated to thermally isolated the temperature control elements (2) from the solid substrate (1), and as such optimise the heat transfer towards the anchoring layer (5). An auxiliary top layer (4) can be implemented to electrically isolate said temperature control elements (2) from a liquid environment (10), and to improve heat conduction to (and from) said anchoring layer and its immediate environment. Said auxiliary top and bottom layers can be multilayers or patterned multilayers to optimise the implementation of their specifications. For example, the temperature control elements can be embedded into a layer that maximises both downward and lateral thermal resistivity, and provides only directly upward, toward the anchoring layer, a good thermally conducting path. Wells (9) can help to further confine heat flow for the duration of the binding event. Care has to be taken that said temperature control structures and auxiliary layers do not interfere with proper functioning of the device. For example, in the field of DNA micro-arrays/chips, the device, which is disclosed in the fourth embodiment, could thermally spot various DNA probes using metal Joule dissipative heaters. However, DNA hybridisation is generally detected using fluorescent labels. If care is not taken, the metal of the heaters could quench the fluorescence signal. An adequately thick dielectric auxiliary top layer could mitigate said problem.

In reference to the fourth embodiment, the solid substrate (1) can comprise Si, GaAs, polymers, glass, .... Said auxiliary bottom layer (3) can comprise an oxide, such as $SiO_2$, or an (oxy)nitride, such as $Si_3N_4$, or a polymer, such as SU-8, BCB, .... Given the requirements—e.g. electrical isolation, thermal conductance, no quenching of fluorescence, resist corrosion in liquid environments, ...—a preferred, but not exclusive, material for the auxiliary top layer (4) is $Ta_2O_5$, since it exhibits such beneficial characteristics, as mentioned in the embodiments disclosed above. However, said auxiliary top layer can comprise other dielectrics, such as $SiO_2$, $Si_3N_4$, ... (for e.g. lateral thermal isolation), and/or polymers, ...). Since they can easily be integrated with microelectronics, and their materials are generally compatible with microelectronics production processes Joule dissipators are a preferred embodiment of heating temperature control elements (2). Non-restrictive examples of Joule dissipators are FETs made in Si, GaAs, ... technology, and resistive heaters comprising metals, such as Pt, Au, Cu, Al, Ta, Ti, Ni, Cr, ..., or semiconductors, such as poly-Si, (doped) Si, (doped) GaAs, .... Temperature sensors (11) are preferably, but not restrictively, integrated using RTDs, because of their simplicity in design and function, their ease to be fabricated/integrated with microelectronics, their fast and sensitive response, their stability and their possibility to create a structure that can simultaneously be used as heater and sensor (and as such facilitates the implementation of a temperature feedback control). The resistance of materials used to implement RTDs, is preferably linearly dependent on the temperature within the envisioned temperature range. An example of such a material of which the resistance exhibits a highly sensitive linear dependence on temperature, is Pt (positive temperature coefficient $\alpha \approx 3850$ ppm/° C. from $-200°$ C. to $600°$ C.). Other materials for RTDs include Ni and Cu.

The anchoring layer (5) of the fourth embodiment answers to the same requirements, specifications and issues as the anchoring layer of the second embodiment. Diels-Alder or Michael addition reactions are the preferred immobilisation reaction schemes, and since said fourth embodiment aspires only thermal spotting, choosing which part of the immobilisation complements should make up the immobilisation sites on the anchoring layer is less restricted.

Example 5

Combined Deposition Control and Sensor Structure

Figure 6:
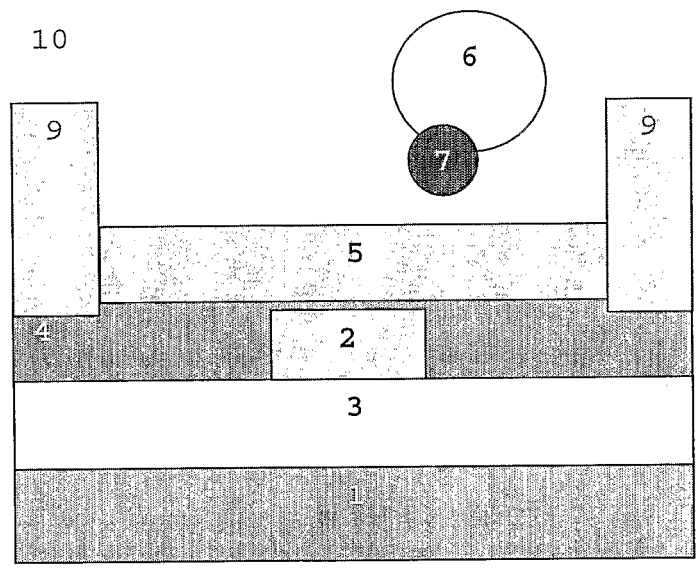

A fifth embodiment discloses a device as depicted in FIG. 6. Said device can be used for electrochemical spotting of molecules (6) by means of a microelectrode (2). Besides being a deposition control element for electrochemical spotting, said microelectrode can also serve as a sensor in for example amperometry, conductometry, impedimetry, voltammetry, and potentiometry, .... Said microelectrode should have electrical access to the electro-active moieties in the anchoring layer (5), meaning that the oxidation state of said electro-active moieties can be changed by said microelectrode, for instance by electron transfer in a redox reaction controlled by said microelectrode. An auxiliary bottom layer (3) can be implemented to electrically isolate said microelectrode from the solid substrate (1). An auxiliary top layer(s) (4) can be implemented to provide binding sites for the anchoring layer by creating a surface more susceptible to an appropriate type of surface chemistry treatment. Said auxiliary top layer(s) can furthermore protect said microelectrode and/or said device from degradation by e.g. electrochemical corrosion in wet operating conditions. Said auxiliary top layer(s) can also electrically isolate said device from e.g. an electrolytic wet environment by covering the surface—and thus the electrical leads running to the microelectrodes—of said device except for the immobilisation spots. Said auxiliary top layer(s) can cushion the sensitivity of said microelectrode. Wells (9) can be implemented to coarsely localise the molecules (6) during the immobilisation binding event and thereby reduce the required volumes of said molecules for immobilisation. By covering the surface of the device except for the immobilisation spots, said wells can further help to electrically isolate said device and protect it from degradation in e.g. wet operating conditions. By providing a dispensing cavity, said wells can also reduce the required volumes of an analyte during sensor operation.

Referring to the fifth embodiment, said microelectrode can comprise a metal (e.g. Pt, Au, Cu, Al, Ti, W, Ta, ...), a (un)doped semiconductor (e.g. Si, GaAs, ...), (un)doped poly-crystalline Si, a conducting polymer (e.g. polyaniline, ...), .... Said auxiliary bottom layer can comprise a dielectric (such as $SiO_2$, $Si_3N_4$, $Ta_2O_5$, ...), or a polymer (e.g. SU-8, BCB, poly-imide, ...). Said auxiliary top layer(s) can comprise oxides (such as $SiO_2$, $Ta_2O_5$, $TiO_2$, ...), (oxy)nitrides (e.g. $Si_3N_4$, ...), polymers (e.g. BCB, SU-8, polyimide, Teflon, ...), conducting polymers, .... Seen its beneficial characteristics as mentioned in previous embodiments, $Ta_2O_5$ is again a preferred material for said auxiliary top layer(s). However, since said microelectrode needs to have electrical access to the electro-active moieties in said anchoring layer, the electrical properties of any auxiliary top layer in between said microelectrode and said anchoring layer is paramount. For example, the thickness of any electrically isolating layer between said microelectrode and said anchoring layer should be limited. Said thickness should preferably be less than 10 nm to allow tunnelling of electrical current. Said wells can comprise polymers, such as BCB, SU-8, Teflon, polyimide, parylene, PDMS, ....

Since the device of the fifth embodiment is aimed at electrochemical spotting, the anchoring layer (5) should therefore comprise electro-active moieties of which the oxidation state can be altered by said microelectrode. Said electro-active moieties make up the immobilisation sites onto which the molecules (6) can bind by preferably Diels-Alder and Michael addition reactions, as in the previous embodiments. Non-restrictive examples of said electro-active moieties are dienophiles (e.g. quinone, maleimide, ...) for Diels-Alder reactions, and $\alpha,\beta$-unsaturated systems (aldehyde, quinone, maleimide, ...) for Michael addition reactions. The spacers of the organic anchoring layer can comprise aliphatic and/or aromatic moieties, but, unless they are conjugate systems, they should be limited in length to assure electrical access. In order to enable electron-transfer, chemical functions—i.e. mediators—can be incorporated into the organic anchoring layer to overcome misalignment of the energetic levels of said microelectrode and the electro-active moieties.

Example 6

Combination of 4 and 5

Another embodiment combines the microelectrode of the fifth embodiment with a local temperature control element as disclosed in the fourth embodiment.

Example 7

Array of Multiple Sensing Devices

In another embodiment a device is disclosed that comprises multiple deposition control elements and/or functional elements (e.g. sensors, ...) on the same solid substrate to constitute an array.

In reference to all previous embodiments, the (bio)molecules (6) that have to be immobilized on the anchoring layer, can be probes for biosensor applications such as single DNA strands, antibodies, enzymes, . . . , or probes sensitive to e.g. ions or light. Furthermore, said molecules can be functional molecules used in the field of molecular electronics, e.g. molecular switches, molecular wires, molecular transistors. Also, said molecules can be molecules used in the field of nanotechnology. Said molecules should have a reactive moiety (7) that can specifically bind to the immobilization sites present on the anchoring layer by means of a locally controllable reaction scheme. The nature of said reactive moiety depends on the type of chemical function used as immobilization site. Non-restrictive examples of reactive moieties and their complementary counterparts are silanes for an oxide (—OH group) anchoring layer, thiols for a metal (Au, Pt, . . . ) anchoring layer, dienes (e.g. cyclohexadiene, cyclopentadiene, . . . ) for dienophiles (quinone, maleimide, . . . ) or dienophiles for dienes (Diels-Alder reaction scheme) nucleophiles (—SH, —$NH_2$, . . . ) for $\alpha,\beta$-unsaturated functions (e.g. aldehyde, quinone, maleimide, . . . ) or $\alpha,\beta$-unsaturated functions for nucleophiles (Michael addition reaction scheme). These reactive moieties can be inherently present in said molecules, e.g. —SH, —NH2, . . . . Otherwise said molecules have to be derivatised and said reactive moiety has to be synthesized onto said molecule.

In reference to all previous embodiments, said device can readily be manufactured by a person skilled in the art by using standard processing steps known in integrated circuit manufacturing used for the production of microelectronic devices.

Disclosed hereafter is a preferred embodiment to create an organic anchoring layer. From liquid or vapour phase, a self-assembled monolayer (SAM) or self-assembled mixed monolayer is formed on the surface of the device, i.e. the auxiliary top layer, the individually addressable deposition control structures or the functional structures, or a combination of the previous. This first layer comprises anchoring molecules with basically three functions: a binding group, a spacer and a functional endgroup. Covalently binding molecules are preferred to ensure long-term stability. The spacer properties strongly affect the kinetics of the self-assembly process and the intralayer stacking of the resulting SAM. The functional endgroup can tune the hydrophobicity of the SAM to control non-specific adsorption or can provide a reactive group so that the anchoring SAM constitutes a precursor or immobilisation site for a subsequent organic layer. Mixed SAMs of anchoring molecules with different functional endgroups and/or spacers can be used to tailor the surface characteristics to various needs, e.g. prevent non-specific adsorption while still providing sufficient immobilisation sites for the subsequent layer.

A second monolayer can be grafted from the anchoring SAM by in-situ chemistry or physisorption from liquid or vapour (e.g. molecular layer epitaxy) phase. Next to a lower binding and an upper reactive linker group, the reagent may comprise auxiliary functional groups that allow control over molecular dipole moments and/or frontier orbital energy levels. Hence, this second layer simultaneously can offer immobilisation sites for the subsequent layers or molecules and can fine-tune the opto-electronic properties of functional structures underneath (e.g sensors).

Depicted in FIG. 7, an exemplary embodiment of an organic anchoring layer is given for a metal or III-V surface. By comprising the two chemical functions depicted in FIG. 7, said organic anchoring layer is a mixed self-assembled monolayer (SAM) that simultaneously offers electro-active hydroquinone (HQ) immobilisation sites, and a number of ethylene glycol (EG) groups (n equals preferably 4, 5 or 6) to resist non-specific adsorption. The immobilisation site HQ has to be oxidised to quinone (Q) before it can react with a diene (i.e. Diels-Alder reaction scheme) or with e.g. a thiol (i.e. Michael addition reaction scheme). The length of the aliphatic spacer determines the stacking quality of the SAM (the longer the better) but also the electrical resistance between the surface and HQ (the shorter the lower), and as such a compromise (e.g. n=11 or 12) has to be made. The aliphatic spacer could also be replaced by an aromatic or (partially) conjugated spacer. By balancing the number of —$CH_2$— and -EG- groups in the immobilisation molecule (FIG. 7, on the left) and the molecule against non-specific adsorption (FIG. 7, on the right), an optimum can be found between providing a well stacked SAM and reducing steric hindrance for the immobilisation binding reaction. Said anchoring layer can also be anchored onto an oxide surface via e.g. EDC/NHS activated coupling onto a (3-Aminopropyl)triethoxysilane.

The method for patterned deposition of the molecules that have to be immobilised can generally be described in several consecutive steps:

In a first step, the immobilisation sites of the anchoring layer are activated if they are not inherently reactive. Said activation can be done across the entire device or locally.

In a second step, the molecules are deposited from liquid or vapour phase. Said molecules can be deposited uniformly across the device or can be coarsely localised on the targeted spots by e.g. dispensing from (micro) syringes/pipettes.

In a third step, the reaction conditions are locally satisfied and for an adequate duration the molecules are allowed to react with the immobilisation sites.

In a fourth step, the molecules that have not reacted with the immobilisation sites together with their deposition phase, are removed from the surface of the device by e.g. washing and rinsing.

Next, if multiple types of molecules have to be immobilised, the previous steps are repeated and cycled for every type of molecule. However, if during the first step activation has occurred across the entire device, this step can be skipped in subsequent cycles.

The order of the previous steps can be altered. For example, local activation of the immobilisation site can be done during the third step, just prior to or during the binding event, after deposition of the molecules.

A slightly different cycle is used for desorption processes. Molecules are then allowed to react across the entire device and then desorbed locally.

Disclosed hereafter is an embodiment to achieve localised immobilisation based on the Diels-Alder/Michael addition reaction scheme. The following details pertain to the first and third step of the immobilisation process as disclosed above. Two types of spotting can be discerned:

in the case of electrochemical spotting, the immobilisation sites are activated in the first step by electrochemical means as known to a person skilled in the art. For example, the deposition control structures (e.g. microelectrode) can be used as working electrodes in a voltammetric three-electrode-setup. The individual deposition control structures are electronically addressed by applying a reducing or oxidising voltage, thereby changing the oxidation state of the electro-active moieties in the anchoring layer, i.e. the immobilisation sites. The deposition control structures are biased such that the immobilisation sites are activated on the targeted spot, e.g. hydroquinone to quinone, and are inhibited on the other spots, e.g. (hydro)quinone to hydroquinone. During the third step, the heat necessary for the Diels-Alder or Michael addition reaction event to occur, is supplied by either heating the entire device (e.g. on hotplate, or global on-device heaters, . . . ) or by local heating using the thermal deposition control structures on the device. If the immobilisation sites cannot be electrochemically activated/inhibited throughout the entire binding event, care has to be taken to dispense the molecules and/or to conduct the binding reaction in a non-oxidising ambient in order not to activate any inhibited spots.

in the case of thermal spotting, the immobilization sites are activated by chemical agents or by electrochemical means. For example, the non-reactive moiety hydroquinone can be oxidised to a quinone, and thus become an immobilisation site, by using chemical agents such as a stream of air or $O_2$ bubbled through a liquid, $I_2$, 2,3-dichloro-5,6-dicyano-1,4-benzoquinone (DDQ) or ceric ammonium nitrate (CAN), . . . . Said chemical activation can be done across the entire device or (coarsely) locally by e.g. dispensing the chemical agents $I_2$, DDQ, or CAN locally. Global/local electrochemical activation can be achieved by e.g. biasing all or individual electrochemical deposition control elements, if present, with an oxidising potential. During the third step, the heat necessary for the Diels-Alder or Michael addition reaction event to occur, is locally supplied by individually addressing the thermal deposition control structures on the device, and as such the binding event only occurs on the locally heated spots.

Several applications of the disclosed device can be thought of, therefore the following enumeration is non-exhaustive. The device as disclosed in the first and second embodiment, can for example be used as an array of enzymatic ISFETs to detect e.g. different neurotransmitters released by neuronal cultures, or to create an electronic nose/tongue, or to electronically detect DNA hybridisation, to create an array of active electrodes to monitor electrically active cells, . . . . The fourth embodiment of the device can be applied in the field of e.g. DNA micro-arrays. The fifth embodiment can be used to construct an array of ion sensitive/selective electrodes with e.g. different enzymes, or to construct an array of passive electrode with various surface chemistry coatings to monitor electrically active cells or the secretion of various chemical substances, that can be enzymatically catalysed.

The invention claimed is:

1. A sensing device for sensing a specific binding between an analyte and a recognition molecule, the sensing device comprising:

a patterned, localized, and individually addressable microelectronic sensor, the sensor comprising:
  a solid substrate,
  a bottom auxiliary layer atop the solid substrate,
  an individually addressable thermal activation element atop a first portion of the bottom auxiliary layer, wherein the individually addressable activation element is configured to activate a sensor surface of the sensing device,
  a top auxiliary layer atop the individually addressable thermal activation element and a second portion of the bottom auxiliary layer not covered by the individually addressable thermal activation element,
  an anchoring layer comprising electroactive moieties, wherein the anchoring layer is situated atop the top auxiliary layer, and wherein there is electrical access between the electroactive moieties and the individually addressable thermal activation element,
  a plurality of self-aligned recognition molecules covalently bound atop the anchoring layer, wherein the self-aligned recognition molecules are configured to bind to an analyte in a binding event, wherein the anchoring layer with the plurality of self-aligned recognition molecules covalently bound thereto is the sensor surface, wherein the individually addressable thermal activation element is configured to adjust a temperature of a part of the anchoring layer and the anchoring layer's immediate surroundings by heating or cooling, wherein the part of the anchoring layer has an area of less than 1 $mm^2$, wherein a volume of the part of the anchoring layer's immediate surroundings, measured as extending into a space accessible by the recognition molecules, is less than 1 $mm^3$, and wherein the sensor is configured to electrochemically detect a specific binding between the recognition molecules and the analyte, and
  wells atop the top auxiliary layer, wherein the anchoring layer is situated between the wells, and wherein the wells are configured to confine a heat flow that occurs between the self-aligned recognition molecules and the anchoring layer for a duration of a binding event.

2. The sensing device of claim 1, wherein the patterned, localized, and individually addressable microelectronic sensor comprises a field effect transistor.

3. The sensing device of claim 1, comprising a plurality of sensor surfaces, wherein each sensor surface is individually addressable and individually activatable.

4. The sensing device of claim 1, comprising a plurality of patterned, localized, and individually addressable microelectronic sensors.

5. The sensing device of claim 1, wherein the anchoring layer is selected from the group consisting of chemical molecules and a metal layer.

6. The sensing device of claim 1, wherein the thermal activation element is selected from the group consisting of a resistor, a microwave heatable element, and a peltier element.

7. The sensing device of claim 1, wherein the device is a microelectronic chip.

8. The sensing device of claim 1, wherein the individually addressable thermal activation element is a field effect transistor attached gate side down to the bottom auxiliary layer.

9. The sensing device of claim 8, wherein the top auxiliary layer is a dielectric layer having a thickness of less than 10 nm, whereby electrical access to the anchoring layer by tunneling is permitted.

10. The sensing device of claim 8, wherein the top auxiliary layer is a metal layer.

11. The sensing device of claim 8, further comprising at least one deposition control structure comprising a temperature control element selected from the group consisting of Joule dissipative heaters and peltier elements.

12. The sensing device of claim 11, further comprising a local temperature sensor configured to monitor a heating/cooling process and to provide control feedback for applied thermal power.

13. The sensing device of claim 11, wherein the auxiliary bottom layer is configured to thermally isolate the temperature control element from the solid substrate and to assist in heat transfer towards the anchoring layer, and wherein the auxiliary bottom layer comprises at least one material selected from the group consisting of an oxide, an oxynitride, and a polymer.

14. The sensing device of claim 11, wherein the top auxiliary layer is an oxide layer providing binding sites for a silane-immobilized anchoring layer.

15. The sensing device of claim 1, wherein the individually addressable thermal activation element is an ion sensitive field effect transistor having an exposed floating gate, and wherein the ion sensitive field effect transistor is positioned with the exposed floating gate adjacent to the top auxiliary layer.

16. The sensing device of claim 15, wherein the top auxiliary layer is a $Ta_2O_5$ layer.

17. The sensing device of claim 1, wherein the self-aligned recognition molecules are of a formula:

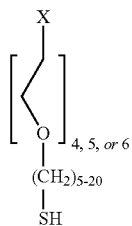

wherein X is OH, $OCH_3$, or hydroquinone.

18. The sensing device of claim 1, wherein the electrical access is an ohmic contact or a diode-like contact between the individually addressable thermal activation element and the electroactive moieties of the anchoring layer.

19. The sensing device of claim 1, wherein the top auxiliary layer and the bottom auxiliary layer are configured to isolate a channel layer of the field effect transistor from a liquid or an electrolyte.

20. The sensing device of claim 1, wherein at least one of the top auxiliary layer and the bottom auxiliary layer is configured to passivate an underlying layer or structure.

21. The sensing device of claim 1, wherein the top auxiliary layer is configured to cushion a sensitivity of a sensor underneath.

22. The sensing device of claim 1, wherein the top auxiliary layer comprises binding sites for the anchoring layer.

23. The sensing device of claim 2, wherein the top auxiliary layer and the bottom auxiliary layer are configured to isolate a channel layer of the field effect transistor from a liquid or an electrolyte.

* * * * *

UNITED STATES PATENT AND TRADEMARK OFFICE
CERTIFICATE OF CORRECTION

PATENT NO.       : 8,758,688 B2
APPLICATION NO.  : 10/583640
DATED            : June 24, 2014
INVENTOR(S)      : Koen De Keersmaecker It is certified that error appears in the above-identified patent and that said Letters Patent is hereby corrected as shown below:

In the Specification

In column 6 at line 16, Change "daring" to --during--.

In column 11 at line 6, Change "control" to --control.--.

In column 13 at line 44, Change "dome" to --done--.

In column 21 at line 19, Change "scheme)" to --scheme),--.

Signed and Sealed this
Twentieth Day of January, 2015

Michelle K. Lee
*Deputy Director of the United States Patent and Trademark Office*